United States Patent [19]

Wong et al.

[11] Patent Number: 5,474,069
[45] Date of Patent: Dec. 12, 1995

[54] NMR LOCAL COIL FOR BRAIN IMAGING

[75] Inventors: Eric C. Wong, Wauwatosa; James S. Hyde, Dousman, both of Wis.

[73] Assignee: The MCW Research Foundation, Inc., Milwaukee, Wis.

[21] Appl. No.: 319,178

[22] Filed: Oct. 6, 1994

Related U.S. Application Data

[62] Division of Ser. No. 6,219, Jan. 9, 1993, Pat. No. 5,372,137.

[51] Int. Cl.⁶ .......................... A61B 5/055; G01R 33/48
[52] U.S. Cl. .................. 128/653.5; 324/318; 324/322
[58] Field of Search ........................ 128/653.2, 653.5; 324/309, 318, 322

[56] References Cited

U.S. PATENT DOCUMENTS

| | | | |
|---|---|---|---|
| 4,304,933 | 12/1981 | Vavrek et al. | 324/318 |
| 4,774,468 | 9/1988 | Bydder | 128/653.5 |
| 4,939,465 | 7/1990 | Biehl et al. | 324/318 |
| 4,992,737 | 2/1991 | Schnur | 324/318 |
| 5,177,442 | 1/1993 | Roemer | 324/318 |
| 5,185,576 | 2/1993 | Vavrek et al. | 325/318 |
| 5,235,279 | 8/1993 | Kaufman et al. | 324/318 |
| 5,281,918 | 1/1994 | Lehr | 324/322 |
| 5,293,126 | 3/1994 | Schaefer | 324/318 |
| 5,372,137 | 12/1994 | Wong et al. | 128/653.5 |
| 5,379,767 | 1/1995 | Derby et al. | 128/653.5 |

OTHER PUBLICATIONS

*High-Resolution, Short Echo Time MR Imaging of the Fingers and Wrist with a Local Gradient Coil*, Radiology 1991; 181:393–397, E. C. Wong, et al.

*Coil Optimization for MRI by Conjugate Gradient Descent*, Magnetic Resonance in Medicine 21, 39–48 (1991), E. C. Wong, et al.

Primary Examiner—Krista M. Zele
Attorney, Agent, or Firm—Quarles & Brady

[57] ABSTRACT

A local RF and gradient coil for acquiring images of the human brain using fast NMR pulse sequences includes an end capped RF bird cage coil surrounded by a 3 axis gradient coil assembly. An RF shield is disposed between the RF coil and the gradient coils and it is divided into separate segments to reduce eddy currents induced by the changing gradient fields.

7 Claims, 6 Drawing Sheets

NMR LOCAL COIL FOR BRAIN IMAGING

This is a division of application Ser. No. 006,219, filed Jan. 19, 1993, now U.S. Pat. No. 5,372,137.

BACKGROUND OF THE INVENTION

The field of the invention is nuclear magnetic resonance imaging methods and systems. More particularly, the invention relates to a local RF and gradient field coil for acquiring NMR images of the human brain.

Any nucleus which possesses a magnetic moment attempts to align itself with the direction of the magnetic field in which it is located. In doing so, however, the nucleus precesses around this direction at a characteristic angular frequency (Larmor frequency) which is dependent on the strength of the magnetic field and on the properties of the specific nuclear species (the magnetogyric constant $\gamma$ of the nucleus). Nuclei which exhibit this phenomena are referred to herein as "spins".

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$, which is rotating, or spinning, in the x-y plane at the Larmor frequency. The practical value of this phenomenon resides in the signal which is emitted by the excited spins after the excitation signal $B_1$ is terminated. There are a wide variety of measurement sequences in which this nuclear magnetic resonance ("NMR") phenomena is exploited.

When utilizing NMR to produce images, a technique is employed to obtain NMR signals from specific locations in the subject. Typically, the region which is to be imaged (region of interest) is scanned by a sequence of NMR measurement cycles which vary according to the particular localization method being used. The resulting set of received NMR signals are digitized and processed to reconstruct the image using one of many well known reconstruction techniques. To perform such a scan, it is, of course, necessary to elicit NMR signals from specific locations in the subject. This is accomplished by employing magnetic fields ($G_x$, $G_y$, and $G_z$) which have the same direction as the polarizing field $B_0$, but which have a gradient along the respective x, y and z axes. By controlling the strength of these gradients during each NMR cycle, the spatial distribution of spin excitation can be controlled and the location of the resulting NMR signals can be identified.

The concept of acquiring NMR image data in a short time period has been known since 1977 when the echo-planar pulse sequence was proposed by Peter Mansfield (J. Phys. C.10: L55–L58, 1977). In contrast to standard pulse sequences, the echo-planar pulse sequence produces a set of NMR signals for each RF excitation pulse. These NMR signals can be separately phase encoded so that an entire scan of 32, 64 or 128 views can be acquired in a single pulse sequence of 20 to 100 milliseconds in duration. The advantages of echo-planar imaging ("EPI") are well-known, and there has been a long felt need for apparatus and methods which will enable EPI to be practiced in a clinical setting. Other echo-planar pulse sequences are disclosed in U.S. Pat. No. 4,678,996; 4,733,188; 4,716,369; 4,355,282; 4,588,948 and 4,752,735.

These fast NMR data acquisition techniques are characterized by the need for rapidly switched gradient fields. As a result, such pulse sequences are not clinically used with commercially available NMR imaging systems because the whole-body gradient coils cannot be switched at the required rate with the available gradient power amplifiers. This is due primarily to the large size and high inductance of such gradient coils. In addition, the high switching rates produce excessive rates of change in the magnetic field in the region of the patient's heart when the patient's head is positioned in the isocenter of the whole-body gradient coils. This FDA limitation on rate of change in magnetic field requires a lowering of the gradient switching rate and a resulting loss in image resolution and/or image quality.

Similarly, the whole-body RF coils provided with commercially available NMR imaging systems are not adequate for EPI imaging. They provide a large field of view to accommodate, for example, the chest and abdominal regions of a human subject, and as a result, their fields couple to large amounts of tissue outside the region of interest being imaged. This lowers the quality factor ("Q") of the RF coil and reduces the signal-to-noise ratio ("SNR") of its signal.

It is well known that the SNR of the RF coil can be significantly improved if it is reduced in size and designed to couple solely with tissues in the region of interest. Such "local" or "surface" coils have been designed for various parts of the human anatomy, such as knees, shoulders, neck, breasts, hands and head. Of particular relevance to the present invention are local head coils which employ the so-called "bird cage" RF coil described by C. E. Hayes et al *J. Magn. Reson.* 63, 622–628 (1985).

Similarly, the power required to drive gradient coils at high switching rates can be reduced significantly if they are reduced in size to produce a uniform gradient field only in the region of interest. Thus, local gradient coils have been designed for various parts of the human anatomy such as the wrist, E. C. Wong et al *Radiology* 181, 393–397 (1991).

SUMMARY OF THE INVENTION

The present invention relates to a local gradient and RF coil which is optimized for acquiring images of the human brain, and particularly, for acquiring images with fast NMR pulse sequences. The local coil includes an end capped bird cage RF coil which surrounds the cranium of the subject, a circular cylindrical RF shield which surrounds the RF coil, and a circular cylindrical gradient coil assembly which surrounds the RF shield and which includes separate coils for producing three orthogonal magnetic field gradients within the region surrounded by the RF coil.

One aspect of the present invention is an RF coil which is optimized for imaging of the human brain. By employing an end cap on the bird cage coil the RF field is more uniform within the volume of the brain, and a maximum filling factor is provided for a short axial length coil. This improves the SNR of images of the brain. A further improvement is provided by configuring the bird cage coil elements in an elliptical shape that conforms more closely to the cranium than the usual circular shape. This also enables the space between the RF coil and the surrounding circular cylindrical RF shield to be greater along each side of the cranium.

Related to this elliptical shape is the manner in which the RF coil is connected to provide a quadrature field. More specifically the quadrature fields are revolved 45° such that each orthogonal RF field is oriented diagonally. Since the major axis of the elliptical RF coil is oriented vertically, this diagonal orientation insures that the quadrature RF fields are symmetrically loaded.

Another aspect of the present invention is the reduction of eddy currents in the local coil assembly due to the gradient fields. The end cap and the end ring of the RF coil are open circuited such that no significant gradient eddy current loops are formed at the frequency of the gradient field changes. Similarly, the RF shield is comprised of separate foil segments that are insulated from each other at the gradient field frequencies. These separate foil segments and the RF coil elements operate as continuous conductive units at the Larmor frequency due to the capacitive coupling between their separate segments and elements.

Another aspect of the present invention is the accurate production of three orthogonal gradient fields within the volume defined by the RF coil and the ability to switch these fields at rates employed in fast NMR pulse sequences.

It is a general object of the present invention to provide a local RF and gradient coil which is optimized for imaging the human brain using fast NMR pulse sequences. The size and shape of the RF coil is such that its field couples with the brain, but not other parts of the anatomy which would lower its Q. The gradient coils are designed to produce accurate gradient fields only within the brain and their inductance is low enough that they can be switched at high rates without excessive power from the gradient amplifiers.

Another object of the invention is to provide a local gradient coil which does not require significant restraint. The x-axis and y-axis gradient coils are disposed symmetrically about the plane z=0. As a result, the gradient fields do not interact with the homogeneous polarizing field to produce any net torque on the local gradient coil which requires physical restraint. Similarly, the z-axis gradient coil is anti-symmetrical about the same plane and no net torques are produced thereby even if the polarizing field lacks homogeneity along the z-axis.

Yet another object of the invention is to provide a local gradient head coil which can be positioned when the patient is outside the magnet bore. Because physical restraints are not required, the head coil can be supported on the patient table which is moved into the bore after the patient is properly positioned. Indeed, the head coil and the patient table may be constructed to guide the head coil into position around the patient's head and firmly support it during the scan.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
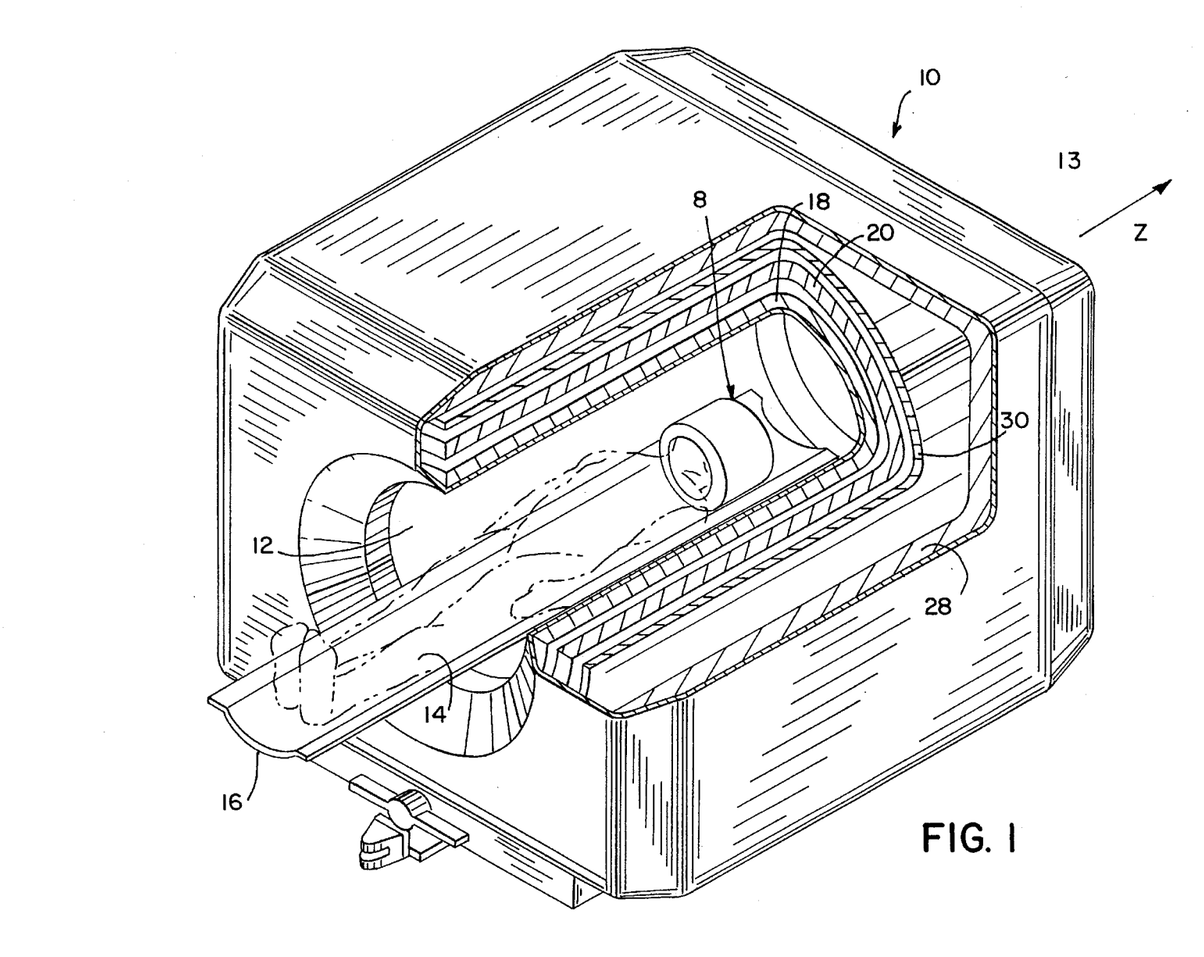
FIG. 1 is a perspective view with parts cut away of an NMR system which employs the present invention.

Referring to FIG. 1, an MRI magnet assembly 10 has a cylindrical bore tube 12 extending along a z-axis 13 for receiving a supine patient 14 supported on a table 16. The table 16 may move in and out of the bore tube 12 so as to position the patient 14 along the z-axis 13 within the volume of the bore tube 12.

Coaxially surrounding the bore tube 12 is a whole-body RF coil 18 for exciting the spins of the patient 14 into resonance, as has been described. Whole-body gradient coils 20 surround both the bore tube 12 and the RF coil 18 and are also coaxial with the z-axis 13, to provide x, y and z gradient fields $G_x$, $G_y$ and $G_z$ as required for MRI imaging. The gradient coils 20 are driven by gradient amplifiers (not shown). The polarizing magnetic field $B_0$, aligned with the z-axis 13, is generated by a superconducting magnet coil 28 coaxial with but outside the bore tube 12, the RF coil 18, and the gradient coils 20. The superconducting magnet coil 28 has no external power supply but operates on an initial current which continues unabated in the zero resistivity windings of the superconducting magnet coil 28.

Interposed between the superconducting magnet coil 28 and the gradient coil 20 is a set of shim coils 30 which are used to correct the homogeneity of the polarizing field $B_0$ as is understood in the art. A set of mechanical linkages and insulators (not shown) rigidly connect each of these coils 18, 20, 28 and 30 together to the bore tube 12 so as to resist relative motions generated by the interaction of their various electromagnetic fields.

When the local coil assembly 8 is used in a general purpose system such as that described above, the whole-body gradient coils 20 and whole-body RF coil 18 are disconnected. The local coil assembly is connected to the x, y and z gradient amplifiers (not shown) on the NMR system and it is connected to the system's transceiver through a transmit/receive switch. For a more detailed description of the entire NMR system and the manner in which the local coil assembly is used therein, reference is made to the copending U.S. patent application Ser. No. 08/005,723 filed on even date herewith and entitled "Time Course MRI Imaging of Brain Functions". It can be appreciated that the local coil assembly 8 may also be used with magnet assemblies specifically designed for head imaging. Such magnet assemblies may have higher field strengths, but they need not be as large in physical size.

The local coil assembly 8, of the present invention, has a circular cylindrical shape and is sized to be received within the bore tube 12 when mounted on the table 16. The inside diameter of the bore tube 12 is approximately 22 inches whereas the inside of the local coil assembly 8 is elliptical in shape and sized to fit closely around the cranium of the subject 14. Thus, the internal volume of the local coil assembly 8 more nearly approaches the volume of the patient's brain.

The local coil assembly 8 is not directly attached to the bore tube 12 but rather is attached to the table 16 and thereby facilitates the alignment of the patient within the local coil assembly 8. The table 16 may be moved along the z-axis 13 to position the local coil assembly 8 at the center of the bore tube 12, generally the position of greatest field homogeneity for the polarizing magnetic field $B_0$. As will be described in more detail below, one of the advantages of the local coil assembly 8 is that it is symmetrically designed such that its interaction with the powerful polarizing magnetic field does not produce any significant net force or torque that might move the assembly 8 during the scan. The local coil assembly 8 need not be physically restrained by attachment to the magnet assembly 10. As a result, the local coil assembly 8 may be applied to the patient's head while the patient is readily accessible outside the bore 12, and mechanical guides can be formed on the table 16 and the local coil assembly 8 to facilitate this procedure.

Figure 2:
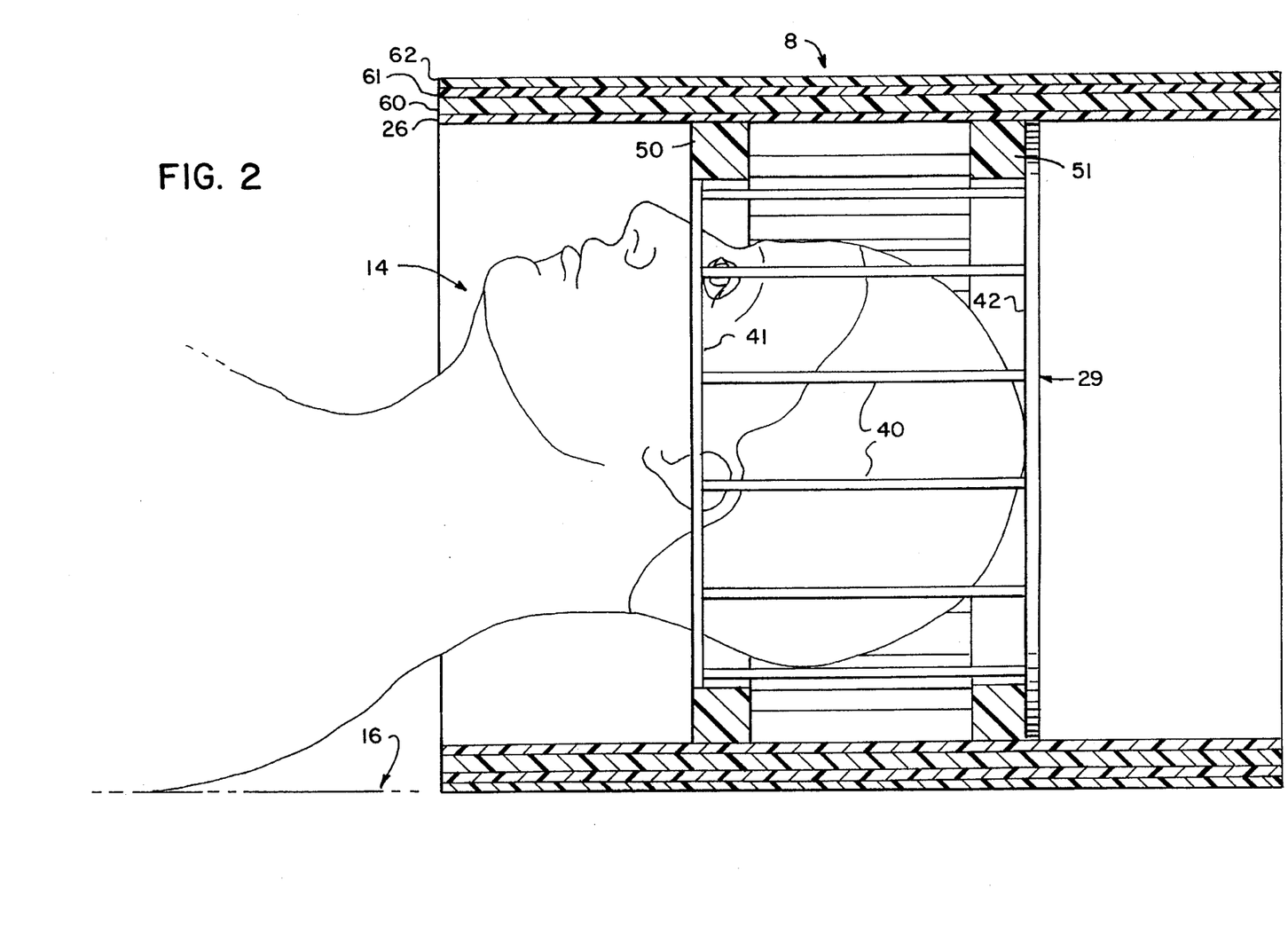
FIG. 2 is a partial elevation view with parts cut away of the subject positioned in the local coil of the present invention.
Figures 3, 4, 5:
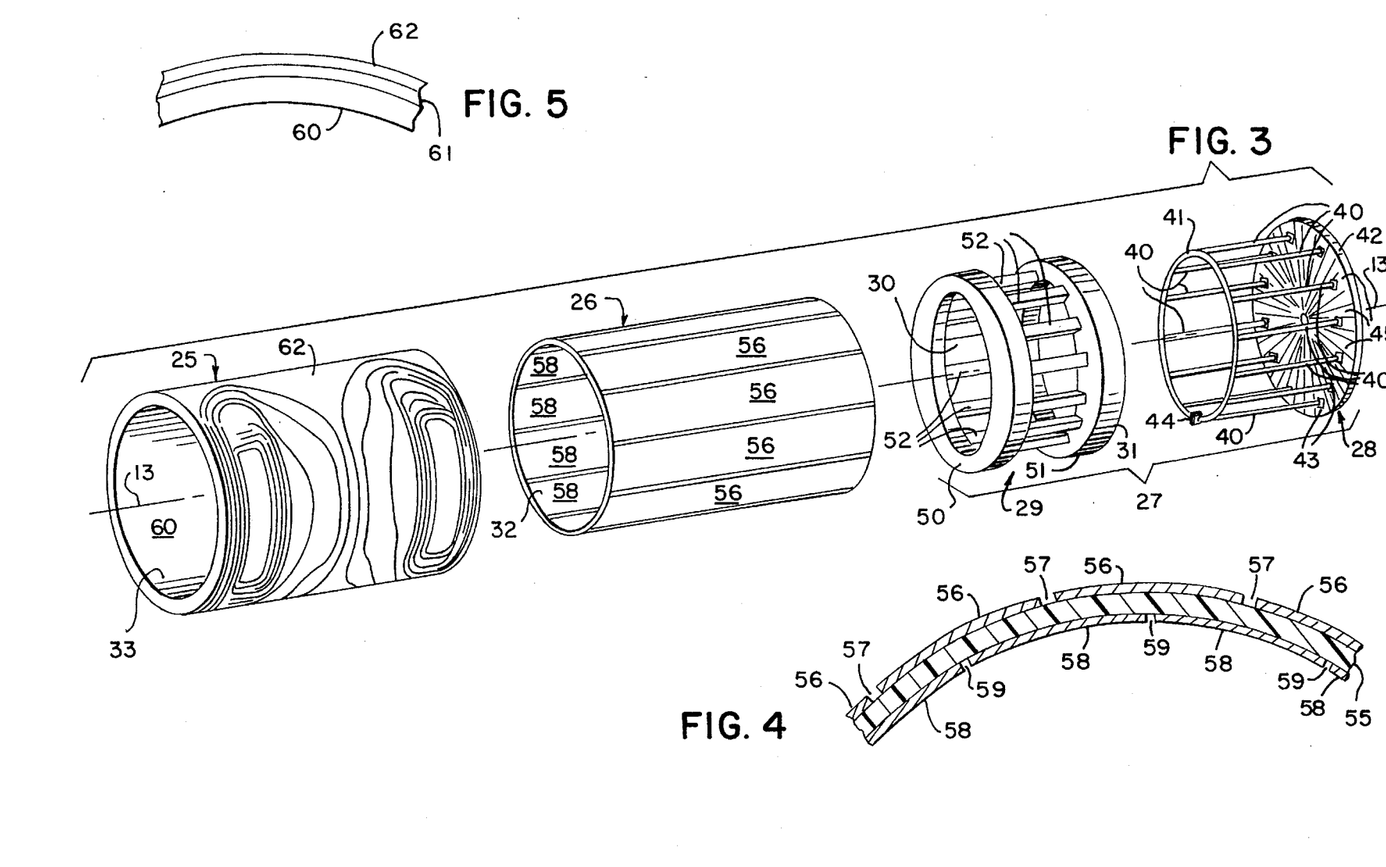
FIG. 3 is an exploded perspective view of the local coil of FIG. 2.
FIG. 4 is a partial view in cross section of the shield assembly which forms part of the local coil of FIG. 3.
FIG. 5 is a partial view in cross section of the gradient coil assembly which forms part of the local coil of FIG. 3.

Referring particularly to FIGS. 2 and 3, the local coil assembly 8 is comprised of three modular assemblies: a gradient coil assembly 25; a shield assembly 26; and an RF coil assembly 27. The RF coil assembly 27 is comprised of an end capped, bird cage coil 28 which is supported within a molded plastic support structure 29. The inner opening 30 in the support structure 29 is elliptical in shape to fit snugly around the patient's cranium, whereas its outer surface 31 is circular in shape and fits snugly within the circular opening 32 in the shield assembly 26. The shield assembly 26 in turn fits snugly within the circular opening 33 in the gradient coil assembly 25.

Referring still to FIGS. 2 and 3, the bird cage coil 28 is comprised of a set of twelve linear elements 40 joined at one end by a conductive end ring 41 and joined at the other end by a conductive end cap 42. The linear elements 40 are 15.9 cm in length and are disposed parallel to each other in an elliptical shape having a major axis of 22.9 cm and a minor axis of 19.1 cm. Coil 28 is a 12 element low-pass transmit-receive design, driven symmetrically through capacitive coupling as will be described below. Capacitors 43 at the junction of each linear element 40 and the end cap 42 tune the coil 28 to the 63.86 MHz Larmor frequency, and a capacitor 44 open circuits the end ring 41 at low frequencies. The end cap 42 is circular with a 29.5 cm diameter, and it is broken into thirty-six wedge-shaped conductive segments 45 which are coupled together by capacitors 90. This capacitive coupling, as well as the capacitor 44 in the end ring 41, are essentially open circuits at the relatively low frequency of the gradient field pulses, and essentially short circuit at the much higher 63.86 MHz Larmor frequency of the RF coil 28. Eddy currents induced by the gradient fields are thus minimized by open circuiting all conductive loops in the coil 28 at the relatively low gradient field frequencies.

A number of variations are possible in the construction of the end cap 42. A more uniform conductive sheet is provided if the capacitors 90 are divided into two or three separate rings spaced equally along the radial dimension of the segments 45. In the alternative, the conductive segments 45 may be formed as a copper sheet on one side of an insulating substrate and a similar set of conductive segments may be formed on the other side. The segments are staggered such that those on the other side overlap two of the conductive segments 45 and form capacitors therewith which properly couple the two segments 45 together at the gradient field switching frequencies. The separate conductive segments 45 may also be directly connected together at the center of the endcap 42 without increasing eddy currents.

The size and shape of the RF coil 28 provides a number of performance improvements. The elliptical opening defined by the end ring 41 and linear elements 40 fits closely around the cranium of the average adult patient, enabling the coil 28 to efficiently couple with the patient's brain. The length of the elements 40 is chosen such that the RF coil 28 encloses the cranial volume, but does not extend over the patient's face. This provides three advantages. First, the patient can see beneath the rim of the coil assembly 8 and is less likely, therefore, to suffer claustrophobia. Second, the eyes, ears and nose of the patient are accessible for applying sensory stimulation often required by brain studies. And finally, the RF coil 28 is spaced far enough from the patient's shoulders and neck so as not to couple therewith and unnecessarily reduce the coil's quality factor. In short, the RF coil 28 is shaped and sized such that it has the best coupling possible with the brain, but minimizes coupling with other parts of the body.

The coupling characteristics of the RF coil 28 are further enhanced by the use of the end cap 42. The end cap 42 improves field uniformity and provides a maximum filling factor for a short axial length coil. In addition, the RF field produced by the coil 28 drops off very sharply in the axial direction so that it can be extended downward around the cranium with minimal coupling to the shoulders or chest. Tests have shown a doubling of the SNR of this RF coil 28 over a conventional bird cage head coil for brain imaging.

Figure 6:
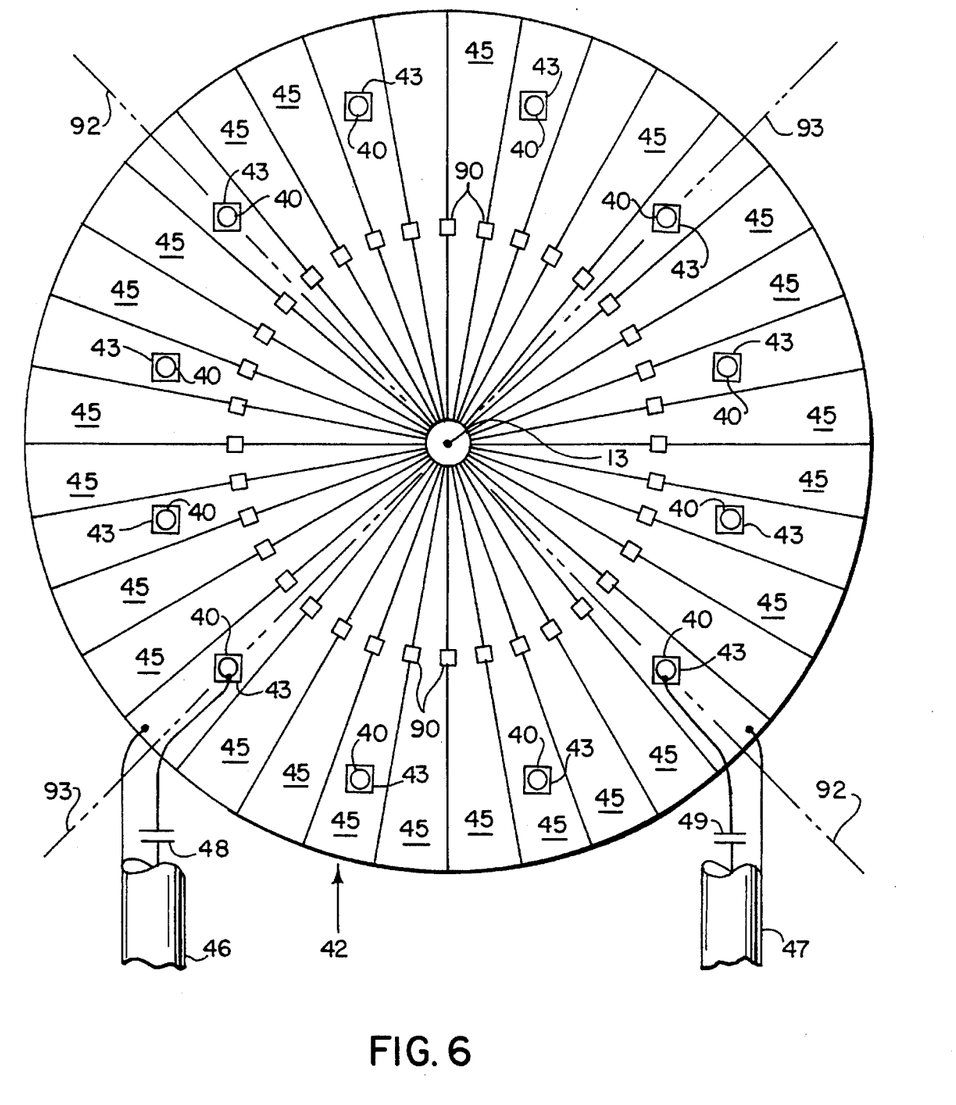
FIG. 6 is a partial view of the RF coil which forms part of the local coil of FIG. 3.

As shown best in FIG. 6, the quadrature signals are applied to and received from the RF coil 28 by a pair of shielded cables 46 and 47. The center leads on cables 46 and 47 are connected through capacitors 48 and 49 to a pair of linear elements 40, which are spaced apart in quadrature with each other and are located on diagonal axes 92 and 93 which intersect the central axis 13. The shields on the cables 46 and 47 connect directly to the corresponding end cap segments 45 which serve as signal ground. The diagonal orientation of the quadrature fields insures that the two signals are equally loaded by the elliptically shaped RF coil 28 and elliptically shaped human head.

The support structure 29 for the RF coil 28 is molded from polyvinyl chloride and it provides the necessary mechanical strength and rigidity for the RF coil elements. It includes a pair of spaced end rings 50 and 51, joined by a set of twelve ribs 52. The ribs 52 house and support the RF coil linear elements 40 and the end ring 50 houses and supports the RF coil end ring 41. The inside surface of the end ring 50 is elliptical in shape to fit closely around the subject's cranium, and the outer surface of both end rings 50 and 51 are circular in shape and sized to fit closely within the RF shield assembly 26. The RF coil assembly 27 is a separate module which may be removed from the local coil assembly 8 and replaced with another RF coil assembly.

As shown in FIGS. 3 and 4, the RF shield assembly 26 is comprised of a circular cylindrical substrate 55 which supports copper foil on both of its surfaces. The outer surface is covered with copper foil segments 56 that are separated by axially directed gaps 57, and the inner surface is covered with copper foil segments 58 that are separated by axially directed gaps 59. The gaps 57 and 59 are staggered such that the copper foil segments 56 and 58 overlap to form a continuous RF shield that surrounds the RF coil assembly 27. The substrate 55 is a dielectric material such as Mylar or Teflon that provides approximately 30 picofarads of capacitive coupling between the foil segments 56 and 58 on its opposite surfaces. This capacitance provides a very low impedance at the relatively high Larmor frequency of the RF coil assembly 27, while presenting a very high impedance at the much lower gradient field pulse rates. Eddy currents induced by the gradient fields are thus minimized by breaking the shield 26 into separate segments, but these segments operate effectively as a continuous RF shield at the Larmor frequency. In the preferred embodiment, each foil is broken into 2 inch wide segments and the RF shield has an axial length of 15 inches. As shown best in FIG. 2, the RF coil 28 is positioned in the center of this shield 26.

Referring particularly to FIGS. 3 and 5, the gradient coil assembly 25 is a circular cylindrical structure comprised of three coil layers 60–62. Each coil layer 60–62 includes an insulating substrate which supports one of the three respective gradient field coils. More specifically, the inner coil layer 60 supports the z-axis gradient coil 65 shown in FIG. 7, the middle coil layer 61 supports the x-axis gradient coil 66 shown in FIG. 8, and the outer coil layer 62 supports the y-axis gradient coil 67 shown in FIG. 9. The inner layer 60 is a polyvinyl chloride pipe cut to 15 inches in length and turned to an outside diameter of 12.375 inches. A groove 0.075" wide and 0.150" deep is cut in the outer surface to receive a pair of 13 gauge copper magnet wires in a z-axis gradient coil pattern described in more detail below.

The middle coil layer 61 is formed by wrapping a layer of epoxy fiber glass around the inner coil layer 60 and turning the outside diameter to 12.575 inches. Grooves 0.075" deep by 0.075" wide are then milled in the outer surface to receive the 13 gauge wire in the x-axis gradient coil pattern described in more detail below. And finally, the outer coil layer 62 is formed by wrapping a layer of epoxy fiber glass around the middle coil layer 61 and turning the outside diameter to 12.775 inches. Grooves 0.075" deep by 0.075" wide are then milled in this turned surface to receive the 13 gauge wire in the y-axis gradient coil pattern described in more detail below.

The local coil assembly 8 may be encapsulated in a suitable housing which provides an aesthetically pleasing appearance and which enables it to be rigidly mounted to the table 16. The interior of the coil assembly may be padded for patient comfort and fit with a firm, open cell foam material.

Figure 7:
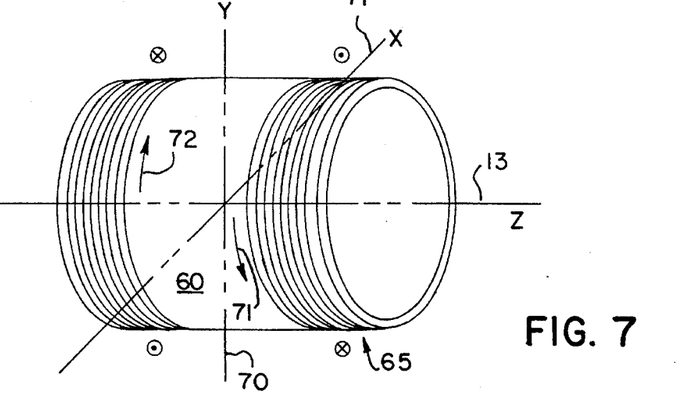
FIG. 7 is a partial perspective view of the z-axis gradient coil which forms part of the gradient coil assembly of FIG. 3.

Referring particularly to FIG. 7, the z-axis gradient coil 65 is comprised of a series of windings that encircle the z-axis 13 and are positioned therealong in a pattern which is anti-symmetrical about a plane through the coil's isocenter (i.e. z=0). The current flows in one direction indicated by arrow 71 in the windings to one side of the isocenter, and it flows in the opposite direction 72 in the windings to the other side of the isocenter. The spacing of these windings along the z-axis are indicated in Table A.

TABLE A

| | |
|---|---|
| z = −7.084" | z = 2.399" |
| z = −6.847" | z = 5.668" |
| z = −6.652" | z = 5.920" |
| z = −6.473" | z = 6.115" |
| z = −6.293" | z = 6.293" |
| z = −6.115" | z = 6.473 |
| z = −5.920" | z = 6.652" |
| z = −5.668" | z = 6.847" |
| z = −2.399" | z = 7.084" |

Grooves are cut along the bottom of the form 60 in the direction of the z-axis 13 to receive the wires that connect the windings together. As indicated above, the z-axis gradient coil 65 contains two #13 wires in each winding and these can be connected in parallel to produce an approximately 2 gauss/cm gradient field, or they can be connected in series to double the number of turns and hence double the gradient field to 4 gauss/cm. The z-axis gradient coil 65 has an inductance of 0.076 mH when connected in parallel, and an inductance of 0.299 mH when connected in series.

Figure 8:
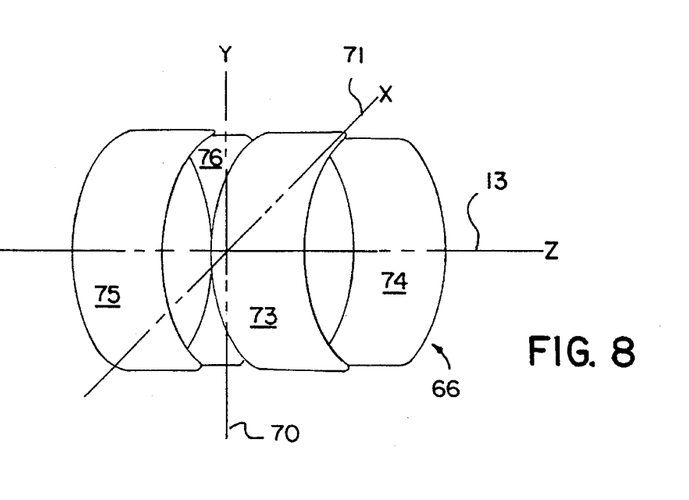
FIG. 8 is a partial perspective view of the x-axis gradient coil which forms part of the gradient coil assembly of FIG. 3.
Figures 10, 11:
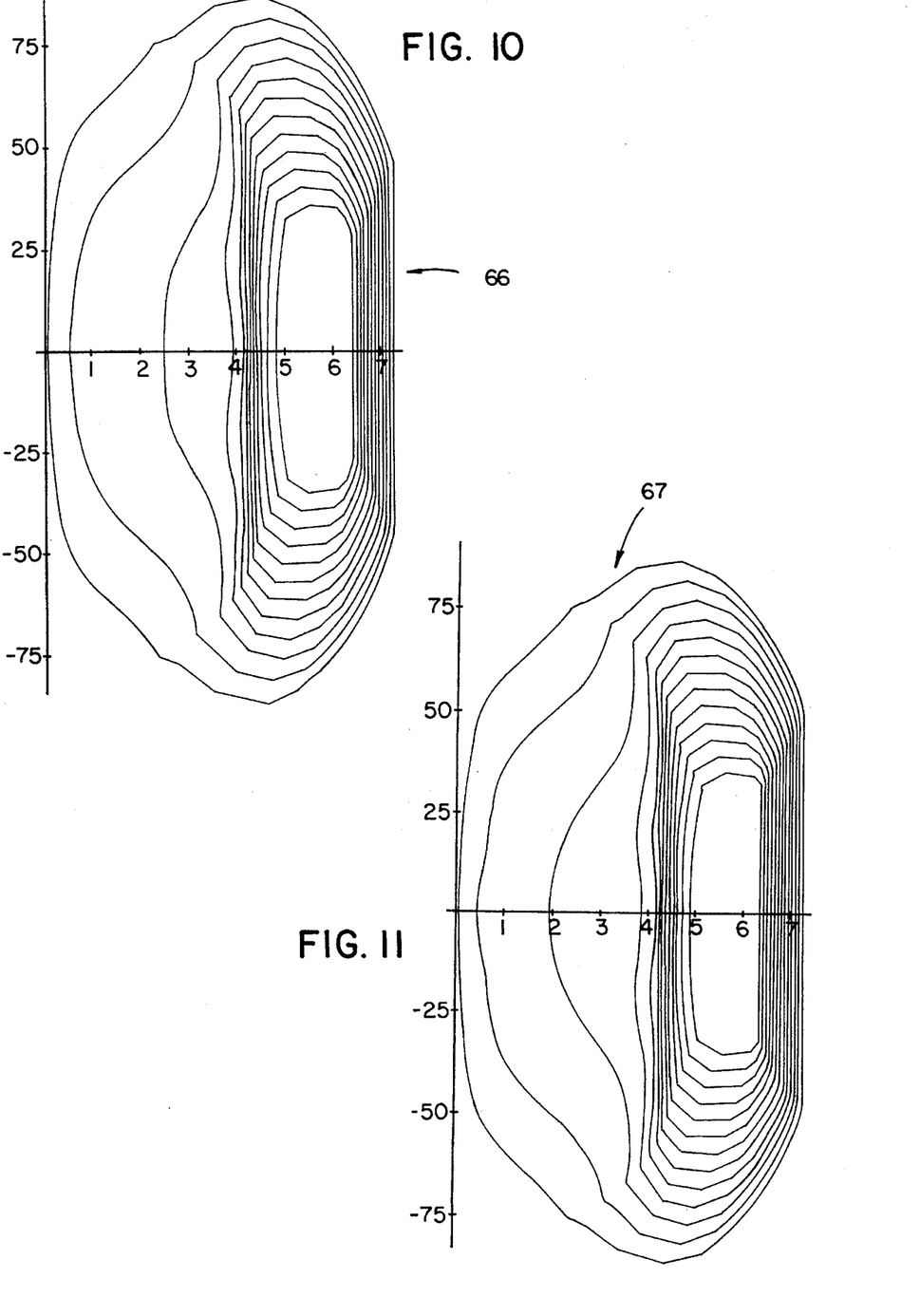
FIG. 10 is a plan view of one pattern in the x-axis gradient coil of FIG. 8.
FIG. 11 is a plan view of one pattern in the y-axis gradient coil of FIG. 9.

Referring particularly to FIGS. 8 and 10, the x-axis gradient coils 66 are formed as four identical patterns 73–76 which are positioned symmetrically about the coil's isocenter located at the intersection of the z-axis 13, y-axis 70 and x-axis 71. The pair of coil patterns 73 and 75 produce a magnetic field along the z-axis 13 in the positive direction and the pair of coil patterns 74 and 76 produce a magnetic field in the opposite direction. These magnetic fields cancel, and are thus zero at the isocenter, but the net field changes linearly as a function of position along the x-axis 71 at a rate of 2 gauss/cm. The x-axis gradient coil has an inductance of 0.144 mH.

Uniformity of this x-axis gradient field is provided by the precise placement of the wires in each pattern 73–76. This placement is shown in FIG. 10 where the horizontal axis measures distance along the z-axis direction from the coil's isocenter and the vertical axis measures circumferential distance around the cylindrical form 61 in degrees. The pattern was calculated using the gradient descent process described by E. C. Wong, A. Jesmanowicz and J. S. Hyde in "Coil Optimization For MRI By Conjugate Gradient Descent," *Magnetic Resonance In Medicine* 21, 39–48 (1991) and incorporated herein by reference.

The four x-axis gradient coil patterns 73–76 are identical and they are positioned on the circular cylindrical support such that they are symmetrical about the z=0 plane through the coil's isocenter. This insures that while forces are produced within the coil assembly 8 when the x-axis gradients are applied, these forces are equal and opposite such that the net force acting on the local coil assembly 8 is substantially zero. Such symmetry has not been achieved in prior local head coils and the resulting forces have caused severe difficulties in securely holding them in place during the scan.

Figure 9:
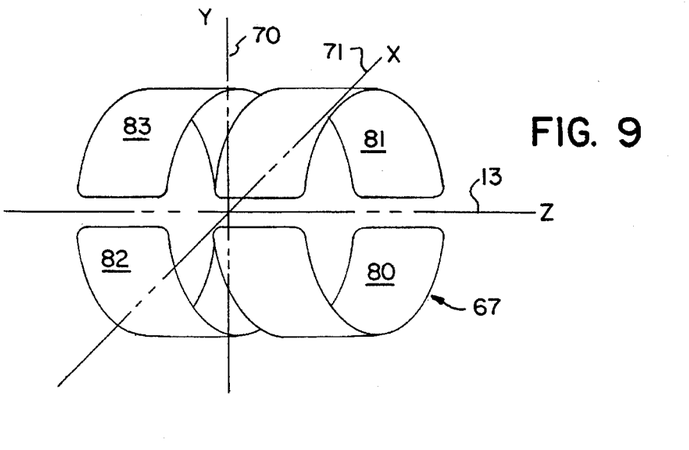
FIG. 9 is a partial perspective view of the y-axis gradient coil which forms part of the gradient coil assembly of FIG. 3.

Referring to FIGS. 9 and 11, the y-axis gradient coils 67 are also formed as four identical patterns 80–83 which are positioned symmetrically about the coil's isocenter. The pair of coil patterns 81 and 83 produce a magnetic field along the z-axis 13 in the positive direction, and the pair of coil patterns 80 and 82 produce a magnetic field in the opposite direction. These magnetic fields cancel, and are thus zero at the isocenter, but the net field changes linearly as a function of position along the y-axis 70 at a rate of approximately 2 gauss/cm.

The y-axis gradient coil has an inductance of 0.174 mH. As shown in FIG. 11, these y-axis coil patterns 80–83 are similar to the x-axis patterns 73–76 since they are designed using the same gradient descent process. Because the y-axis gradient coils 67 are disposed further radially outward from the z-axis 13 than the x-axis gradient coils 66, however, they contain one extra loop in each of the patterns 80–83. The y-axis patterns 80–83 are positioned on the circular cylindrical form such that they are symmetrical about the z=0 plane through the coil's isocenter, and as with the x-axis gradient coils, this prevents the creation of any significant net force on the local coil assembly 8 when the y-axis gradient field is produced.

It should be apparent to those skilled in the art that many variations can be made from the preferred embodiment described above without departing from the spirit of the invention. For example, while a low-pass bird cage RF coil is preferred, a high-pass or a band-pass bird cage coil may also be used. While the elliptical shape is preferred since it approximates the shape of the human head, other shapes are possible as long as they produce a relatively uniform RF field throughout the brain.

We claim:

1. A local gradient coil for use in a polarizing magnetic field for obtaining NMR data from the head of a human subject, which comprises:

a substrate formed about a z-axis to define a volume for receiving the head of the human subject;

a z-axis gradient coil disposed on the substrate for producing a magnetic field gradient along the z-axis;

an x-axis gradient coil disposed on the substrate for producing a magnetic field gradient along an x-axis which is perpendicular to the z-axis; and a y-axis gradient coil disposed on the substrate for producing a magnetic field gradient along the y-axis which is perpendicular to the z-axis;

wherein the three gradient coils are shaped such that:
   a) the three perpendicular magnetic field gradients are uniform throughout an entire region occupied by a brain of the human subject received in said volume;
   b) all three gradient coils are symmetric about the z-axis;
   c) the x-axis and y-axis gradient coils are symmetric about the x-axis and the y-axis;
   d) the z-axis gradient coil is antisymmetric about the x-axis and the y-axis; and
   e) the length of the three gradient coils along the z-axis does not exceed twice the distance from the center of the subject's brain to the subject's shoulders.

2. The local gradient coil as recited in claim 1 in which each of the three gradient coils is formed by conductive paths and the locations of the conductive paths in each of the three gradient coils are determined using a gradient descent process.

3. A local gradient coil for use in a polarizing magnetic field for obtaining NMR data from the head of a human subject, which comprises:

a substrate formed about a z-axis to define a volume for receiving the head;

a z-axis gradient coil disposed on the substrate for producing a magnetic field gradient along the z-axis;

an x-axis gradient coil disposed on the substrate for producing a magnetic field gradient along an x-axis which is substantially perpendicular to the z-axis; and a y-axis gradient coil disposed on the substrate for producing a magnetic field gradient along a y-axis which is substantially perpendicular to the z-axis and x-axis;

wherein the three substantially perpendicular magnetic field gradients are substantially uniform throughout a region occupied by the brain in the head received in said volume; and wherein all three gradient coils are symmetric about the z-axis, the x-axis and y-axis gradient coils are symmetric about the x-axis and the y-axis, and the z-axis gradient coil is antisymmetric about the x-axis and the y-axis such that the net force imposed on the local gradient coil as a result of its interaction with the polarizing magnetic field is substantially zero.

4. The local gradient coil as recited in claim 3 in which the substrate defines a cylindrical volume for receiving the subject.

5. The local gradient coil as recited in claim 3 in which the x-axis, y-axis and z-axis gradient coils are formed from copper wire disposed in groves formed on the substrate.

6. The local gradient coil as recited in claim 3 in which the x-axis gradient coil is formed by four identical coil patterns disposed symmetrically about an isocenter located in the volume.

7. The local gradient coil as recited in claim 3 in which the y-axis gradient coil is formed by four identical coil patterns disposed symmetrically about said isocenter.

\* \* \* \* \*